United States Patent [19]

Fernandez-Acebal et al.

[11] Patent Number: 4,588,119

[45] Date of Patent: May 13, 1986

[54] PROCESS AND APPARATUS FOR OBTAINING INSPECTION SAMPLES FROM WOUND COILS

[75] Inventors: José Fernandez-Acebal; Jürgen Herm; Harald Tomsen, all of Hamburg; Walter Wilms, Duisburg, all of Fed. Rep. of Germany

[73] Assignee: Blohm & Voss AG, Hamburg, Fed. Rep. of Germany

[21] Appl. No.: 716,036

[22] Filed: Mar. 26, 1985

[30] Foreign Application Priority Data

Mar. 26, 1984 [DE] Fed. Rep. of Germany ....... 3411077

[51] Int. Cl.$^4$ ............................................. B26F 3/00
[52] U.S. Cl. ..................... 225/2; 73/864.41; 83/919; 225/96.5; 225/103
[58] Field of Search ................ 225/2, 93, 96.5, 103; 73/864.41; 83/191, 919

[56] References Cited

U.S. PATENT DOCUMENTS 3,495,488  2/1970  Addis et al. ........................... 83/919
3,851,552  12/1974  English et al. ....................... 83/191

Primary Examiner—Frank T. Yost
Assistant Examiner—Hien H. Phan
Attorney, Agent, or Firm—Nils H. Ljungman

[57] ABSTRACT

A method and apparatus are provided for automatically cutting and retrieving for inspection a sample length of coiled material from an inner tab region of a wound coil using a machine having a motorized roller apparatus supporting and driving the wound coil. A machining arm including a cutter is introduced within the wound coil for cutting a given radial thickness of the coiled material in the inner tab region. The machining arm is withdrawn, and a specimen extraction arm having substantially "C"-shaped elements is introduced within the wound coil. The "C"-shaped elements may each have a pointed limb, which in use serves to pry out the sample length of coiled material in the inner tab region, and break the sample length loose from the wound coil in the region of the cut provided by the cutter. The extraction arm is withdrawn when the retrieving elements bring the sample length of coiled material out for inspection.

20 Claims, 3 Drawing Figures

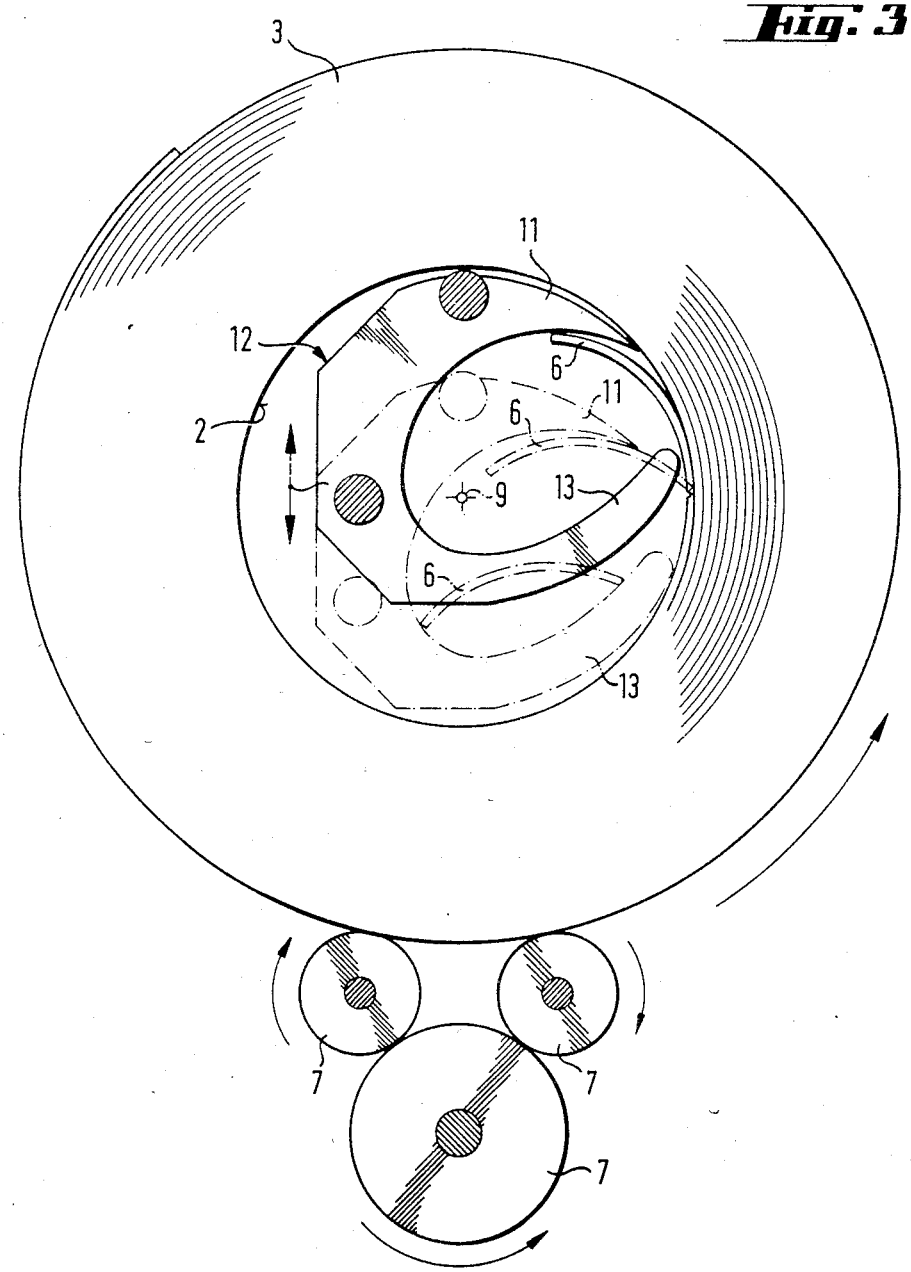

PROCESS AND APPARATUS FOR OBTAINING INSPECTION SAMPLES FROM WOUND COILS

BACKGROUND OF THE INVENTION

1. Field of the Invention

The invention relates to a process and an apparatus for obtaining strip specimens from the area of the strip tabs of strips wound into coils for material inspection.

2. Description of the Prior Art

It is known in the art of metal rolling that certain rolling stresses are imposed during the rolling operation, on the material being rolled. This is generally true of all rolling operations, and it is desirable to know the degree of the rolling stress so as to make an allowance for the same in any future processing or fabrication of the rolled material.

In a process where the rolled material is formed into wound or rolled coils, it is easy enough to subject the rolled material to stress-analysis, by taking a sample length of the rolled material from the exterior or outermost end of the wound coil. However, it is found in practice that rolling stresses imposed on elongate material which is rolled, will almost always vary from the region of the inside tab of the wound coil through a middle region of the wound coil to the outermost region of the wound coil. For this reason, if a sample is taken from the outermost region per se of the wound or rolled coil, which region of the coil is most accessible, any data obtained from analyzing a sample from the outermost region will not represent the stress level of the rolled material in the region of the inside tab of the wound coil.

Also, experience has shown that the extraction of only one specimen on the external circumference of a metal strip which has been wound into a coil does not always give sufficient information on the quality of the entire coil.

The distribution of the exceeding limit of elasticity over the length of the strip is not uniform, because of the processes to which the strip has been subjected. As a rule, the exceeding limit of elasticity of the inside strip tab is greater by a predetermined amount than that of the outside strip tab of the strip wound into a coil. By the precise determination of the limit of elasticity at the beginning of the coil, for example, of the inside strip tab, it is possible to reduce the maximum limit of elasticity. Also, among other things, it is also possible to reduce the costs for the production of hot-rolled wide strip, for example, by using smaller quantities of alloy elements. Basically, it is possible to take and examine specimens at any point over the length of the strip, if the strip has previously been unwound. However, it should be noted that especially with fairly great strip thicknesses and/or with wide high-strength hot-rolled strips, this method cannot be used because such strips cannot be economically wound again after the specimen has been removed.

Hitherto, whenever a sample of the coiled material was required to be taken out from the inside of a wound coil, access to the coil inside was unobtainable in coils with relatively small inside diameters. Samples had to be obtained by opening out or unrolling the coil and re-rolling the coil after sampling. While such an operation satisfied the sampling requirement, the overall process suffered from lack of economy and lack of efficiency in production.

There has been an unfilled need for a process and apparatus wherein a sample from the inside tab region of a wound coil of metallic material may be automatically obtained in a short period of time without opening the coil for obtaining a sample specimen for inspection.

OBJECT OF THE INVENTION

The object of the invention is therefore to provide an apparatus and process with the capability of taking specimens from strips which have been wound into coils, specifically from the coil inside at a region which is the beginning of the coil, without having to completely unwind the coil before it is used or reprocessed, for example, for the manufacture of a helical welded tube.

SUMMARY OF THE INVENTION

This objective is achieved by taking for inspection one or more strip tabs from the inside or the free axial area of the coil comprising the rolled-up strip.

The invention in its broad form comprises an apparatus for automatically cutting and retrieving for inspection a predetermined sample length of coiled material from an open inner periphery of a wound or rolled coil of elongate material, said coil being wound in a machine having means for supporting said coil, said apparatus comprising: machining means having a cutter for cutting said coiled material within said inner periphery; means for causing relative motion between said coiled material and said machining means for introducing said cutter within said inner periphery of said coiled material; said cutter, being disposed when introduced within said inner periphery, for cutting a predetermined thickness of a portion of said coiled material at a predetermined location on said inner periphery of said coiled material; and specimen extraction means for bending said predetermined sample length of said coiled material at said predetermined location of said cutting, for breaking said predetermined sample length of said coiled material and for retrieving said predetermined sample length of said coiled material.

Also described and claimed herein is a process for obtaining an inspection sample from the inner periphery of a coil of wound strip material.

BRIEF DESCRIPTION OF THE DRAWINGS

A more detailed understanding of the invention may be had from the following description of a preferred embodiment, to be read and understood in conjunction with the accompanying drawings wherein:

FIG. 3 shows a section, also perpendicular to the axis of the coil, with an apparatus to break off and remove the strip tab from the inside of the coil.

DESCRIPTION OF THE PREFERRED EMBODIMENT

A preferred process and apparatus according to the invention are described herein below, with reference to FIGS. 1 to 3.

Figure 1:
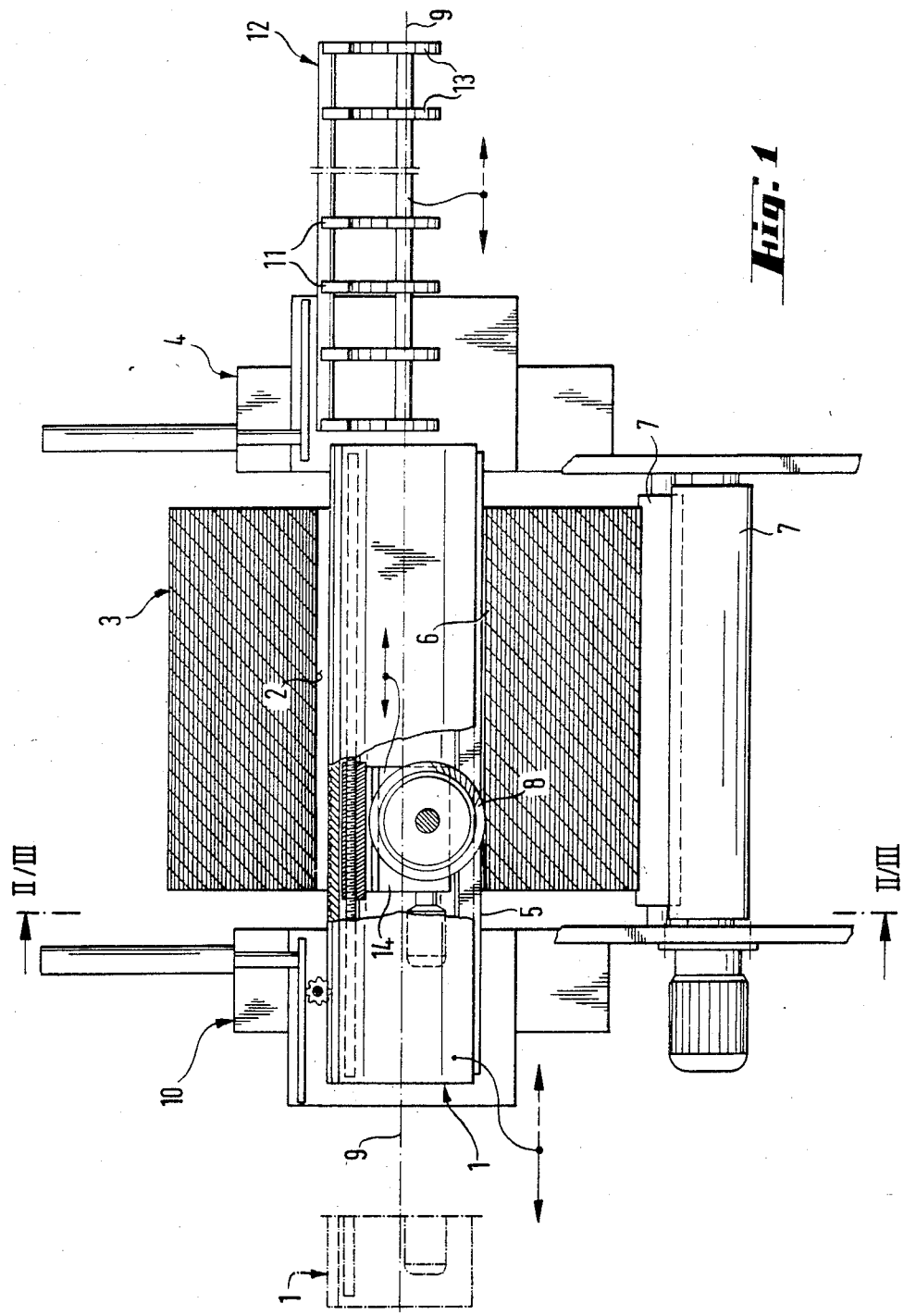
FIG. 1 shows a vertical section in the plane of the axis of a coil with an apparatus for the extraction of a strip tab to be inspected, coming from the inside end of the strip, using the invention.
Figure 2:
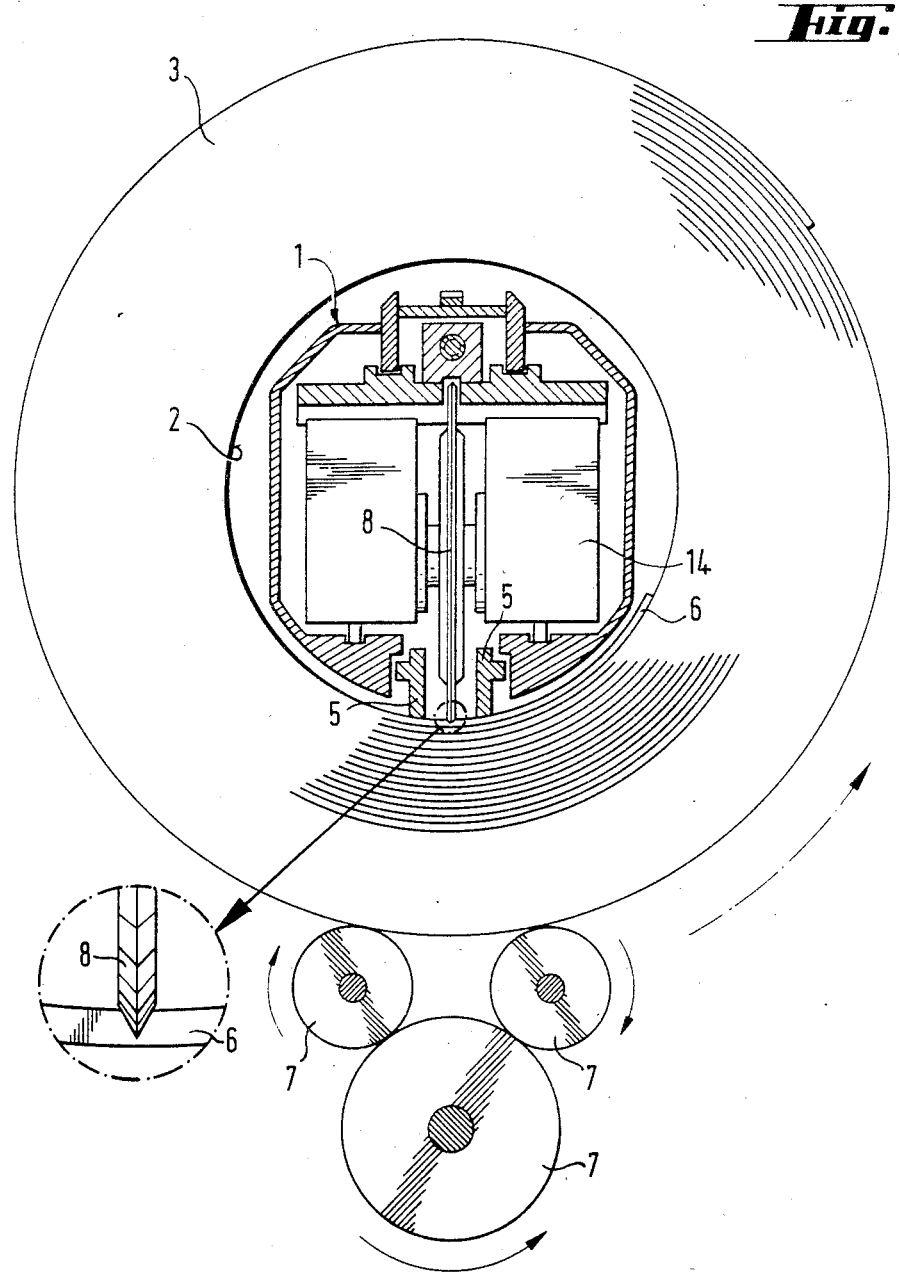
FIG. 2 shows a section perpendicular to the axis of the coil with an apparatus for milling a groove in the strip tab on the inside end of the strip.

Referring first to FIG. 1, the coil 3 is rotated about its axis 9 by means of drive rolls 7 so that the end of the strip tab 6 is substantially in the three o'clock or nine o'clock position (as shown in FIG. 2).

Then, a milling machine arm 1, which may be fitted by means of a light scanner (not shown) to the inside coil diameter 2, is introduced inside the coil 3 through the open end opposite to the main bearing 10. The milling machine arm 1 is lowered on both sides, for example hydraulically, in the end area of the open end support 4 and in the area of the main bearing 10 to lower pressure pads 5. The pressure pads 5 apply pressure preferably over the entire width of the coil on the strip tab 6 in the six o'clock position and are located to the left and right of a cut or milled groove to be formed by a cutter 8. As illustrated in FIG. 2, the cutter has a rotary knife edge. However, other types of cutting edges are conceivable and are within the scope of the invention. The pressure pads 5 are spaced so that the strip layer located underneath is not damaged during the subsequent cutting or milling; for example, a small amount (approximately 0.5–1.0 mm) of the strip thickness of the strip tab 6 to be removed is left uncut and remains behind. The thickness of the pressure pads 5 may be changed depending on the thickness of strip material which is to be cut, and depending on other specific requirements. Any other alternative means other than the pressure pads 5 may be used to hold the strip tab 6 down, and is within the scope of the invention. Such means will be intelligible to those who are skilled in the art.

The milling is preferably carried out with a narrow disc milling cutter 8. The milling machine arm 1 is designed as a guide for the milling apparatus 14 to assist in the operation.

Once again referring to FIG. 1, parallel with the extension of the milling machine arm 1, after the completion of the milling, a specimen extraction arm 12 is inserted into the coil 3 preferably from the other side opposite the main bearing 10, and expediently supported on this opposite side, or may alternately be on the side of the main bearing.

The specimen extraction arm 12, as shown in FIG. 3 in particular, is designed to have a member with a "C"-shaped configuration with an upper leg 11 and a lower leg 13, wherein the upper leg 11 is used for opening and breaking off the strip, and the lower leg 13 is used to receive and catch the strip tab 6 which has been broken off. For this purpose, the coil 3 is rotated so that the milled groove moves from the six o'clock position into the three o'clock or nine o'clock position. As the coil rotates, by virtue of the upper leg 11 of the specimen extraction arm 12, the strip tab 6 is pried away and comes loose from the adjacent strip winding of the coil 3, because of the greatly-reduced cross-section of the strip in the area of the milling.

The specimen extraction arm 12 is then lowered, for example hydraulically, whereby the low residual strip thickness in the area of the milling cut is broken off by the sharpened upper leg 11 and drops onto the lower leg 13 of the specimen extraction arm 12.

The specimen extraction arm 12 is then withdrawn and the separated strip tab 6 is removed, for example by means of a hoist, if necessary. Other alternative configurations for the extraction arm as well as the milling machine arm may be used and are within the scope of this invention.

The foregoing extraction apparatus and method provide an easy, convenient, economical and fast manner of obtaining a sample specimen for analysis from the inside tab region of a wound coil of material. It is to be noted that the angular positions for the location of the pads and the application of the milling cutter, as well as the positions of the specimen extraction arm for the retrieval of the sample specimen in the form of the tab piece dislodged from the inside of the coil, are not unique to the invention and may be suitably chosen by one skilled in the art.

The invention is not to be taken as limited to all of the details thereof, as modifications and variations of the described arrangements may be made without departing from the spirit and scope of the invention.

What is claimed is:

1. A method of automatically cutting and retrieving for inspection a predetermined sample length from an open inner periphery of a wound coil of elongate material, said coil being wound in a coil winding machine having means for supporting said coil, said method comprising:
    inserting machining means into said wound coil inner periphery, said machining means being provided with an actuatable cutter;
    using pressure applying means on said inner periphery to hold at least a portion of said inner periphery in place without motion;
    cutting a predetermined thickness of said coiled material at a predetermined location of said inner periphery of said coil;
    inserting a specimen extraction means into the said inner periphery of said coil and deforming said predetermined sample length of said coiled material at said predetermined location and thereby breaking said predetermined sample length of said coiled material from said coil to form an inspection sample; and
    withdrawing said specimen extraction means to retrieve said predetermined sample length for analysis.

2. The method according to claim 1 including the step of rotating said wound coil in said coil winding machine and obtaining predetermined angular positions of said wound coil before the steps of inserting said machining means, cutting said predetermined thickness of said wound coil, and inserting said specimen extraction means.

3. The method according to claim 2 wherein the said step of deforming said predetermined sample length of said coiled material and breaking said predetermined sample length of said coiled material comprises using at least one substantially "C"-shaped element mounted on said specimen extraction means, said "C"-shaped element having a pointed arcuate upper leg and an arcuate lower leg.

4. The method according to claim 2 wherein the step of using pressure applying means comprises applying two substantially parallelly spaced pressure pads at said inner periphery of said wound coil, said wound coil being disposed horizontally and having a horizontally disposed longitudinal axis, said pressure pads being disposed parallel to said coil axis at substantially at a 6 o'clock position of said wound coil.

5. The method according to claim 4 wherein the step of cutting said predetermined thickness of said coiled material comprises cutting with a rotary cutter.

6. The method according to claim 5 including the step of supporting said coil on drive rollers disposed at a bottom portion of, and contacting said wound coil.

7. Apparatus for automatically cutting and retrieving for inspection a predetermined sample length of coiled material from an open inner periphery of a wound coil of elongate material having a longitudinal axis within said inner periphery, said coil being wound in a machine having means for supporting said coil, said apparatus comprising:

machining means including a cutter for cutting said coiled material within said inner periphery;

means for causing relative motion between said coiled material and said machining means for introducing said cutter within said inner periphery of said coiled material;

said cutter, being disposed when introduced within said inner periphery, for cutting a predetermined thickness of a portion of said coiled material at a predetermined location on said inner periphery of said coiled material; and specimen extraction means having retrieving elements for bending said predetermined sample length of said coiled material at said predetermined location of said cutting, for breaking said predetermined sample length of said coiled material and for retrieving said predetermined sample length of said coiled material.

8. The apparatus according to claim 7 wherein said machining means includes means for applying pressure disposed in use to apply pressure and hold at least a position of said inner periphery along a longitudinal surface parallel to said longitudinal axis of said wound coil.

9. The apparatus according to claim 8 which includes first and second support means for supporting said machining means in a vertical direction at substantially first and second end regions of said wound coil.

10. The apparatus according to claim 8 wherein said pressure applying means comprises strip-like pressure pads which are parallelly spaced.

11. The apparatus according to claim 11 including hydraulic means to lower said pressure pads onto said inner periphery of said wound coil at a 6 o'clock position thereof.

12. The apparatus according to claim 10 including pressure pads of varying thicknesses.

13. The apparatus according to claim 7 wherein said machining means includes a rotary cutter.

14. The apparatus according to claim 13 wherein said rotary cutter includes a cutting knife edge which is circumferential.

15. The apparatus according to claim 7 wherein said supporting means includes supporting drive rollers which are motor driven and disposed in contact with a bottom portion of said wound coil.

16. The apparatus according to claim 7 wherein said retrieving element of said specimen extraction means comprises substantially "C"-shaped elements.

17. The apparatus according to claim 16 wherein each said "C"-shaped element includes a pointed substantially arcuate limb.

18. The apparatus according to claim 17 wherein said specimen extraction means has an axis substantially coincident with said longitudinal axis of said wound coil and wherein said specimen extraction means includes means to impart angular rotation to said "C"-shaped elements to make said pointed arcuate limbs act as mechanical separators.

19. The apparatus according to claim 7 wherein said machining means comprises a milling machine arm, and wherein said cutter comprises a milling cutter.

20. Apparatus for automatically cutting and retrieving for inspection a predetermined sample length of coiled material from an open inner periphery in a region of an inner tab of a wound coil of elongate material, said wound coil being wound in a machine having motorized roller means supporting and rotating said wound coil in use, said apparatus comprising:

machining arm means including a cutter for cutting said coiled material within said inner periphery;

said machining arm means including means to introduce said machining arm means within said wound coil, said machining arm means including means to actuate said cutter for cutting a predetermined radial thickness of said coiled material at a predetermined location proximate said inner tab of said inner periphery of said wound coil; and a specimen extraction arm means including retrieving elements which can be inserted within said wound coil for deforming a predetermined sample length of said elongate material in said region of said inner tab and for breaking loose said predetermined sample length of said elongate material, said retrieving elements substantially having a "C"-shaped configuration, whereby when said specimen extraction arm means is withdrawn from said wound coil, said predetermined sample length of said elongate material can be retrieved for inspection.

* * * * *